United States Patent [19]

Saul et al.

[11] Patent Number: 5,868,743
[45] Date of Patent: Feb. 9, 1999

[54] CARDIAC ABLATION SYSTEM WITH LOW TEMPERATURE TARGET SITE IDENTIFICATION

[75] Inventors: Jerome Philip Saul, Newton, Mass.; Jean-Marc Cote, Beauport, Canada

[73] Assignee: Children's Medical Center Corporation, Boston, Mass.

[21] Appl. No.: 764,318

[22] Filed: Dec. 12, 1996

Related U.S. Application Data

[60] Provisional application No. 60/008,598 Dec. 13, 1995.
[51] Int. Cl.$^6$ .................................................. A61B 17/36
[52] U.S. Cl. .............................................. 606/49; 607/101
[58] Field of Search ................................. 606/41, 48–50, 606/42; 607/100–102, 122; 600/374

[56] References Cited

U.S. PATENT DOCUMENTS

| | | |
|---|---|---|
| 4,785,815 | 11/1988 | Cohen . |
| 5,156,151 | 10/1992 | Imran . |
| 5,450,846 | 9/1995 | Goldreyer .............................. 607/122 |
| 5,540,681 | 7/1996 | Strul et al. .............................. 607/101 |

OTHER PUBLICATIONS

Blouin, L. et al., "Assessment of Effects of a Radiofrequency Energy Field and Thermistor Location in an Electrode Catheter on the Accuracy of Temperature Measurement", *PACE*, vol. 14, pp. 807–813 (1991).

Hoffman, E. et al., "Temperature–controlled Radiofrequency Catheter Ablation of AV Conduction: First Clinical Experience", *European Health Journal*, vol. 14, pp. 57–64 (1993).

Kongsgaard, E. et al., "Power and Temperature Guided Radiofrequency Catheter Ablation of the Right Atrium in Pigs", *PACE*, vol. 17, pp. 1610–1620 (1994).

Lanberg, J. et al., "Temperature Monitoring During Radiofrequency Catheter Ablation of Accessory Pathways", *Circulation*, vol. 86 (5), pp. 1469–1474 (1992).

McRury, I. et al., "Temperature Measurement as a Determinant of Tissue Heating During Radiofrequency Catheter Ablation: An Examination of Electrode Thermistor Positioning for Measurement Accuracy", *Journal of Cardiovascular Electrophysiology*, vol. 6 (4), pp. 268–278 (1995).

Nath, S. et al., "Correlation of Temperature and Pathophysiological Effect During Radiofrequency Catheter Ablation of the AV Junction", *Circulation*, vol. 92 (5), pp. 1188–1192 (1995).

Panescu, D. et al., "Three–Dimensional Finite Element Analysis of Current Density and Temperature Distributions During Radio–Frequency Ablation", *IEEE Transactions on Biomedical Engineering*, vol. 42 (9), pp. 879–890 (1995).

Simmers, T. et al., "Effects of Heating with Radiofrequency Power on Myocardial Impulse Conduction: Is Radiofrequency Ablation Exclusively Thermally Mediated?", *Journal of Cardiovasc Electrophysiol.*, vol. 7, pp. 243–247 (1996).

Wittkampf, F., "Temperature Response in Radiofrequency Catheter Ablation", *Circulation*, vol. 86 (5), pp. 1648–1650 (1992).

Calkins, H. et al., "Temperature Monitoring During Radiofrequency Catheter Ablation Procedures Using Closed Loop Control", *Circulation*, vol. 90 (3), pp. 1279–1286 (1994).

Cote, J. et al., "Low–Temperature Mapping Predicts Site of Successful Ablation While Minimizing Myocardial Damage", *Circulation*, vol. 94 (3), pp. 253–257 (1996).

*Primary Examiner*—Jennifer Bahr
*Assistant Examiner*—Roy D. Gibson
*Attorney, Agent, or Firm*—Thomas J. Engellenner; David A. Lane, Jr.; Lahive & Cockfield, LLP

[57] ABSTRACT

A method of targeting and ablating cardiac tissue wherein an ablation catheter is directed and positioned at a potential ablation site, and is energized to a catheter tip temperature of approximately 50 degrees centigrade while observing whether AP block occurs. If block occurs, the site is confirmed and treatment is then initiated at a higher ablation level, either immediately or at a later time. On the other hand, if block does not occur within a first time interval $T_1$, illustratively five or ten seconds, at the lower targeting energy, the catheter is repositioned and another site evaluated.

11 Claims, 5 Drawing Sheets

| | A | | AV | | V | |
|---|---|---|---|---|---|---|
| | YIELD | VOL | YIELD | VOL | YIELD | VOL |
| 50°C | 9 | 1.1 | 9 | 2.4 | 8 | 2.1 |
| 60°C | 70 | 14.9 | 27 | 14.5 | 36 | 28.0 |
| 70°C | 40 | 15.6 | 63 | 18.4 | 92 | 24.1 |

YIELD, LESION YIELD (%); VOL, VOLUME (mm³)

FIG. 4A

CHARACTERISTICS OF RADIOFREQUENCY APPLICATIONS

| APPLICATION | 50°C TEST | | | | 60°C TEST | | | |
|---|---|---|---|---|---|---|---|---|
| | t_block (sec) | t_off (sec) | t_off - t_block (sec) | t_return (sec) | T_peak (°C) | t_block (sec) | t_off (sec) | t_off - t_block (sec) | t_return (sec) | T_peak (°C) |

| APPLICATION | t_block (sec) | t_off (sec) | t_off-t_block (sec) | t_return (sec) | T_peak (°C) | t_block (sec) | t_off (sec) | t_off-t_block (sec) | t_return (sec) | T_peak (°C) |
|---|---|---|---|---|---|---|---|---|---|---|
| SUCCESSFUL SITES | | | | | | | | | | |
| 1 | 1.0 | 3.0 | 2.0 | 1.8 | 45 | ... | ... | ... | ... | ... |
| 2 | 1.1 | 3.0 | 1.9 | 2.7 | 47 | ... | ... | ... | ... | ... |
| 3 | 1.2 | 5.0 | 3.8 | 6.5 | 44 | ... | ... | ... | ... | ... |
| 4 | 1.6 | 3.0 | 1.4 | 3.3 | 48 | ... | ... | ... | ... | ... |
| 5 | 1.6 | 3.5 | 1.9 | 2.5 | 44 | ... | ... | ... | ... | ... |
| 6 | 1.8 | 3.0 | 1.2 | 3.6 | 45 | ... | ... | ... | ... | ... |
| 7 | 1.9 | 3.9 | 2.0 | 1.7 | 45 | ... | ... | ... | ... | ... |
| 8 | 2.0 | 4.0 | 2.0 | 0.7 | 47 | ... | ... | ... | ... | ... |
| 9 | 2.1 | 3.0 | 0.9 | 1.8 | 48 | ... | ... | ... | ... | ... |
| 10 | 2.7 | 6.2 | 3.5 | 1.9 | 44 | ... | ... | ... | ... | ... |
| 11 | 2.7 | 4.0 | 1.3 | 7.0 | 48 | ... | ... | ... | ... | ... |
| 12 | 2.9 | 4.0 | 1.1 | 5.0 | 45 | ... | ... | ... | ... | ... |
| 13 | 4.5 | 7.2 | 2.7 | 1.9 | 49 | ... | ... | ... | ... | ... |
| 14 | 7.0 | 8.3 | 1.3 | ... | 49 | 8.4 | 10.0 | 1.6 | 1.8 | 58 |
| 15 | ... | 10.0 | ... | ... | ... | ... | ... | ... | ... | ... |
| MEDIAN | 2.0 | 4.0 | 1.9 | 2.7 | 47 | ... | ... | ... | ... | ... |
| MEAN | 2.4 | 4.7 | 1.9 | 3.1 | 46.4 | ... | ... | ... | ... | ... |
| SD | 1.6 | 2.2 | 0.9 | 1.9 | 1.9 | ... | ... | ... | ... | ... |
| UNSUCCESSFUL SITES | | | | | | | | | | |
| 1 | 6.4 | 8.5 | 2.1 | 1.5 | 46 | ... | ... | ... | ... | 53 |
| 2 | ... | 10 | ... | ... | 46 | ... | 10 | ... | ... | 49 |
| 3 | ... | 10 | ... | ... | 44 | ... | 10 | ... | ... | 62 |
| 4 | ... | 10 | ... | ... | 48 | ... | 10 | ... | ... | 55 |
| 5 | ... | 10 | ... | ... | 46 | ... | 10 | ... | ... | 51 |
| 6 | ... | 10 | ... | ... | 45 | ... | 10 | ... | ... | 53 |
| 7 | ... | 10 | ... | ... | 45 | ... | ... | ... | ... | ... |
| 8 | ... | 10 | ... | ... | 48 | ... | ... | ... | ... | ... |
| 9 | ... | 10 | ... | ... | 50 | ... | ... | ... | ... | ... |
| 10 | ... | 10 | ... | ... | 48 | ... | ... | ... | ... | ... |
| 11 | ... | 10 | ... | ... | 46 | ... | ... | ... | ... | ... |
| 12 | ... | 10 | ... | ... | 50 | ... | 10 | ... | ... | 53 |
| MEDIAN | | | | | 46 | | | | | 53.8 |
| MEAN | | | | | 46.8 | | | | | 4.5 |
| SD | | | | | 2.0 | | | | | |

CONTINUE TO FIG. 4B

CHARACTERISTICS OF RADIOFREQUENCY APPLICATIONS

70°C APPLICATION

| APPLICATION | $t_{block}$ (sec) | $t_{off}$ (sec) | $t_{off} - t_{block}$ (sec) | $t_{return}$ (sec) | $T_{peak}$ (°C) |
|---|---|---|---|---|---|
| SUCCESSFUL SITES | | | | | |
| 1 | 1.3 | 60 | 58.7 | : | 55 |
| 2 | 1.6 | 40 | 38.4 | : | 72 |
| 3 | 0.8 | 60 | 59.2 | : | 55 |
| 4 | 1.6 | 64 | 62.4 | : | 67 |
| 5 | 1.3 | 40 | 38.7 | : | 58 |
| 6 | 1.6 | 60 | 58.4 | : | 56 |
| 7 | 0.9 | 60 | 59.1 | : | 63 |
| 8 | 0.7 | 60 | 59.3 | : | 61 |
| 9 | 1.5 | 11 | 9.5 | : | 57 |
| 10 | : | 60 | : | : | 58 |
| 11 | 2.1 | 50 | 47.9 | : | 66 |
| 12 | 1.0 | 42 | 41.0 | : | 66 |
| 13 | 1.5 | 60 | 58.5 | : | 58 |
| 14 | 0.9 | 60 | 59.1 | : | 52 |
| 15 | 1.8 | 60 | 58.2 | : | 70 |
| MEDIAN | 1.5 | 60 | 58.7 | : | 58 |
| MEAN | 1.3 | 52 | 50.6 | : | 60.1 |
| SD | 0.4 | 14 | 14.6 | : | 6.1 |
| UNSUCCESSFUL SITES | | | | | |
| 1 | 3.3 | 60 | 56.7 | 4.8 | 53 |
| 2 | 9.0 | 10 | 1.0 | 3.0 | 58 |
| 3 | : | 10 | : | : | 52 |
| 4 | : | : | : | : | : |
| 5 | : | : | : | : | : |
| 6 | : | : | : | : | : |
| 7 | : | : | : | : | : |
| 8 | : | : | : | : | : |
| 9 | : | : | : | : | : |
| 10 | : | : | : | : | : |
| 11 | : | : | : | : | : |
| 12 | : | : | : | : | : |
| MEDIAN | : | : | : | : | : |
| MEAN | : | : | : | : | : |
| SD | : | : | : | : | : |

CONTINUED FROM FIG. 4A

*FIG. 4B*

CARDIAC ABLATION SYSTEM WITH LOW TEMPERATURE TARGET SITE IDENTIFICATION

RELATED APPLICATIONS

The instant application is related to the copending provisional application Ser. No. 60/008,598, filed on Dec. 13, 1995, entitled "Low Heat Ablation Catheter Mapping", and claims priority therefrom.

BACKGROUND

The present invention relates to cardiac ablation systems, and more particularly to RF ablation systems in which a radio frequency ablation catheter is inserted, typically via a cut down to a major artery or vein, to access the wall of the heart and "ablate" tissue by the application of RF energy thereto. The energy is applied at a level and for a time effective to denature or kill the active tissue and thereby eliminate a region of myocardium or abnormal electrical pathway responsible for an arrhythmia.

A number of techniques have been developed for identifying the relevant sites in the cardiac wall, and for guiding an ablation catheter to the correct site for treatment. In particular, there exist a number of so-called mapping catheters which are inserted to detect and map cardiac signals. These catheters typically have a plurality of electrodes which each are operated in a sensing mode to receive cardiac signals and identify the location of the target site, and have one or more electrode portions which may be actuated to apply energy and treat the site. A reasonable degree of accuracy is achieved by such mapping catheters. Nonetheless, treatment of cardiac sites in this manner remains subject to a number of uncertainties due in part to the inaccuracies of determining the exact lesion site, and in part to the difficulty of applying the correct amount of energy to dependably ablate the site. Ablation is effected by raising the tissue temperature sufficiently high for a suitable length of time. Typically, in current technology, one does not actually measure the tissue temperature achieved in the cardiac wall but only the temperature of the catheter tip or of the electrode portion contacting the wall. This is done, for example by using an ablation catheter such as the Medtronic RF Ablater, which has a temperature sensor centrally located in its electrode tip. Typically, the catheter control console is set to achieve a tip temperature of 70–80 degrees centigrade, with the assumption, based on experimental data, that actual tissue temperatures will be approximately 0–10 degrees centigrade higher. Nonetheless, even at these temperatures, it is not uncommon for conduction to return after a lapse of fifteen to twenty minutes, requiring a second round of targeting and ablation to be undertaken. In addition, ineffective applications which produce these high temperatures may kill areas of heart tissue unnecessarily, and may produce long term risks.

Thus, it would be desirable to develop a method which more accurately identifies a target site and positions an ablation electrode at the site.

If it would further be desirable to identify methods of ablation which are highly effective yet reduce the risk of damaging tissue sites at which block would not occur.

SUMMARY OF THE INVENTION

These and other desirable goals are achieved in a method of targeting and ablating cardiac tissue wherein an ablation catheter is directed and positioned at a potential ablation site, and is energized to bring cardiac tissue at the catheter tip to a temperature of approximately 50 degrees centigrade while observing if block occurs. If block occurs, the site is confirmed and treatment is then initiated, either immediately or at a later time, at a higher ablation temperature level. On the other hand, if block does not occur within a first time interval $T_1$, illustratively ten seconds, at the lower targeting energy, the catheter is repositioned and another site evaluated.

An ablation console implementing the method includes an automated control and detection module which operates in two modes. A first mode used for confirming targeting sites has a set point of approximately 50 degrees and applies a lower level of ablation energy to the catheter electrode with that set point for a time period no more than about ten seconds. Upon receipt of an actuation signal the console then operates in a second mode to apply an ablation level of energy for achieving permanent block. The actuation signal may be an automated signal initiated from conventional cardiac monitoring equipment upon detecting occurrence of block, i.e., the cessation of the conduction signal. Alternatively, the initiation signal may be a trigger signal manually initiated by the physician upon observation of the appropriate electrical response. Thus, the console operates to first apply energy for a time and at a low set point or temperature which does not damage tissue but is effective to achieve at least temporary block, and upon achievement of block applies a greater ablation energy at a higher temperature set point.

In a preferred embodiment, the first mode operates to achieve a tissue temperature below 52 degrees centigrade, and preferably in the range of 48–52 degrees centigrade, while the second mode is a permanent ablation regimen that operates at a higher temperature in the range of 60 or 70 degrees centigrade. The control protocol applies the higher energy only if conduction block is successfully achieved at the lower, non-damaging or reversible, energy level.

In variations of a method for carrying out the present invention, sites successfully blocked at the non-damaging energy level of the first mode, rather than being immediately treated, are mapped, for example, in mapping catheter coordinates, or by fluoroscopic imaging, for later ablation. However, preferably ablation is effected immediately, while the electrode remains in position at the identified and confirmed AP site.

BRIEF DESCRIPTION OF THE DRAWINGS

These and other features of the invention will be understood from the claims below taken together with the figures illustrative of experimental observations and operation of the various aspects of the invention wherein:

FIG. 4 is a Table of targeting and ablation conditions and results in the practice of the invention.

DETAILED DESCRIPTION

Figure 1A:
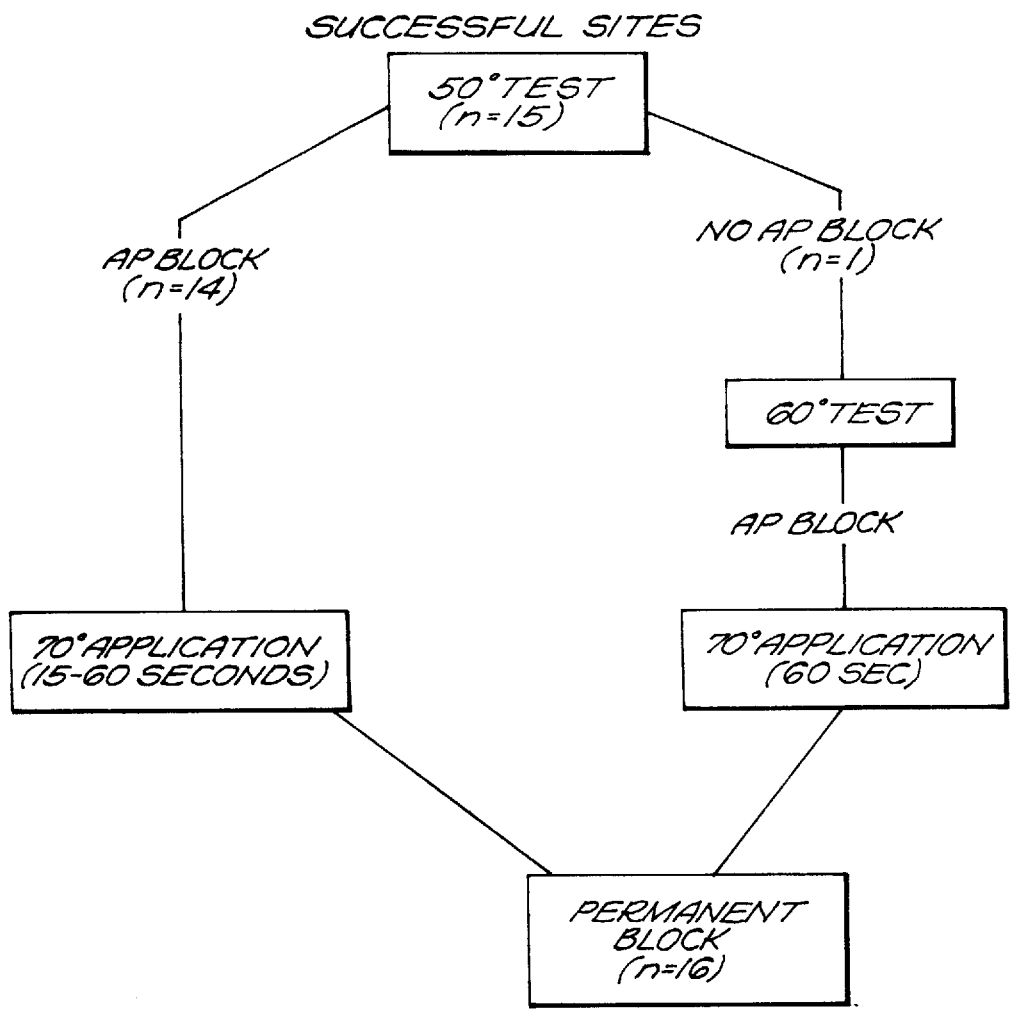
FIG. 1A shows positive results of an experimental procedure identifying and ablating sites using applicant's invention.

Applicant's invention is based on the discovery that by locally "stunning" cardiac tissue by raising its temperature to a low and non-damaging temperature level, one can identify a preponderance of true positive conduction sites, and greatly limit the destruction of false positive or test sites implicit in existing cardiac ablation methods. Essentially temperature-limited RF test applications are applied to achieve AP conduction block, and confirm that the catheter is located at a site requiring treatment. The site is then treated at a higher, ablative, set-point, or mapped for later treatment at the higher level.

According to a principal aspect of the invention, the initial targeting of sites is performed with a level of heating that does not permanently damage the cardiac tissue—i.e. it remains histologically unchanged—but that is effective to block conduction in a tissue region extending several millimeters from the catheter treatment electrode. This involves bringing the tissue to a temperature in the range of 45°–52° C., generally 48°–52° C., which in the prototype embodiments discussed below corresponds to a catheter tip temperature of 44°–49° C., for a time period which is sufficiently short to assure that no permanent damage occurs.

With this treatment, when the electrode is sufficiently near to a conduction path, conduction block sets in as the temperature rises, generally within 3–8 seconds of actuation. Conversely, if block does not occur by a fixed maximum time $T_{off}$, the catheter tip may be assumed to be located such that further ablation would be either ineffective to achieve permanent block or require an excessively large lesion to achieve block, due, for example, to being at least several millimeters away from the required pathway. The interval $T_{off}$ is selected to be sufficiently short that tissue damage does not occur even when the low temperature RF heating is applied for the full interval.

Representative embodiments of treatment protocols and equipment for carrying out the invention will be discussed further below, together with clinical and investigative results of the prototype method.

EXAMPLE 1

Methods

Fifteen symptomatic patients (age, 13.5±6.7 years: range, 5 to 34 years; median, 11.9 years) with single manifest (n=10) or unidirectional retrograde (n=5) accessory pathways (APs) were studied. AP locations were left free wall for 8 patients, right free wall for 1, and posteroseptal for 6. Informed written consent was obtained from each patient/parent. An atrial approach to the atrioventricular groove was used for all APs (transseptal for left-sided). APs were mapped in either sinus rhythm, atrial pacing, orthodromic tachycardia, or ventricular pacing. Target sites were selected on the basis of local atrial or ventricular activation times, the presence of both atrial and ventricular electrograms, and occasionally the presence of an AP potential. All ablations were performed with a steerable 7F quadripolar electrode catheter (Marinr, Medtronic CardioRhythm) with a 4 mm distal platinum electrode and a thermocouple embedded in its center for temperature monitoring (essentially the "RF Ablatr" depicted in FIG. 1 of the Calkins, H. et al. article, Circulation Vol. 90, No. 3 September 1994 pp. 1279–1286). All applications were performed with a Medtronic radiofrequency generator (Atakr, Medtronic CardioRhythm) in its temperature control mode, in which the generator automatically modulates the delivered power between 0.5 to 5.0 W using feedback from the catheter-embedded thermocouple to attempt to achieve a selected target temperature of between 45° C. and 95° C.

Ablation and Temperature Mapping Protocol

At identified target sites, a low-temperature test application was performed with the radiofrequency generator set initially to 50° C. The test application was continued for a maximum of 10 seconds or until evidence of AP conduction block was noted. If either AP conduction returned or 15 minutes passed, a second radiofrequency application was made with a 70° C. set point at the same site for a maximum of 60 seconds. If the initial low-temperature 50° C. test application was unsuccessful, a similar 60° C. test application was given to determine if absence of AP block was due to incorrect catheter position or inadequate heating. Any test application that resulted in AP block was followed by a 70° C. application that was continued for a maximum of 60 seconds. Target sites of eventual permanent success, defined as no return of AP conduction prior to the end of the procedure, are referred to as 'successful' sites. Target sites at which either AP conduction never blocked or conduction returned after a 70° C. application of 10 seconds or longer are termed "unsuccessful" sites.

Statistical Analysis

Data are presented as mean±SD. Comparisons between the ablation parameters obtained at the same sites were performed with the paired Student's t test, while comparisons between different sites were performed with the unpaired Student's t test. A value of $P<0.05$ was considered significant.

Results

Figure 1B:
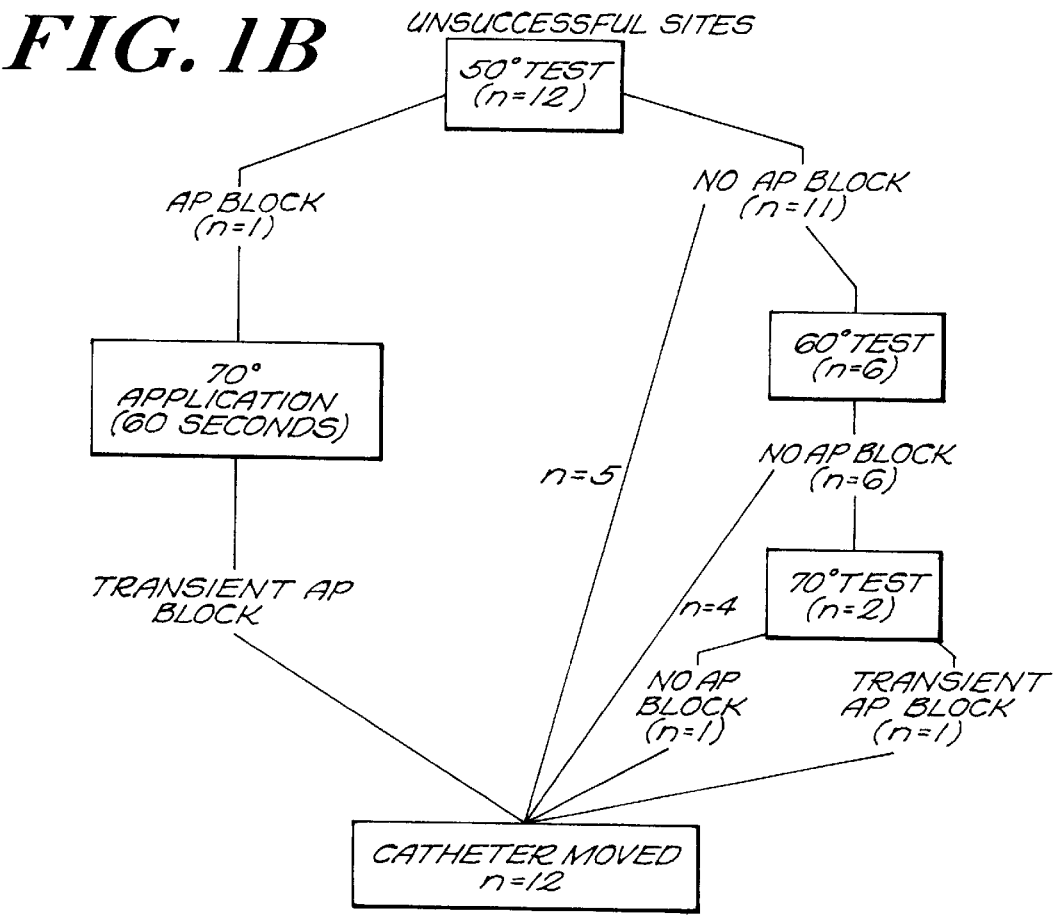
FIG. 1B shows results for unsuccessful ablation sites using the confirmation protocol of applicant's invention.

Radiofrequency catheter ablation was successful in all 15 patients. Radiofrequency energy was delivered to a total of 27 target sites, 15 successful and 12 unsuccessful. Seven patients had AP conduction block and successful ablation at the first target site, whereas the other 8 had AP conduction block and successful ablation after failure at 1 to 4 other target sites. Although 50° C. test applications were delivered at all successful and unsuccessful sites, due to protocol deviations, higher temperature test applications were delivered at only 7 of the 12 unsuccessful sites (n=6 at 60° C.; n=2 at 70° C.). FIGS. 1A and 1B set forth the protocols and number of sites for the successful (FIG. 1A) and unsuccessful (FIG. 1B) sites. FIG. 4 is a Table showing the detailed treatment regimens, temperatures, and times until block was achieved. No differences were found for the characteristics of test applications by pathway location; however, there were only two right freewall applications.

Successful Sites

Figure 2A:
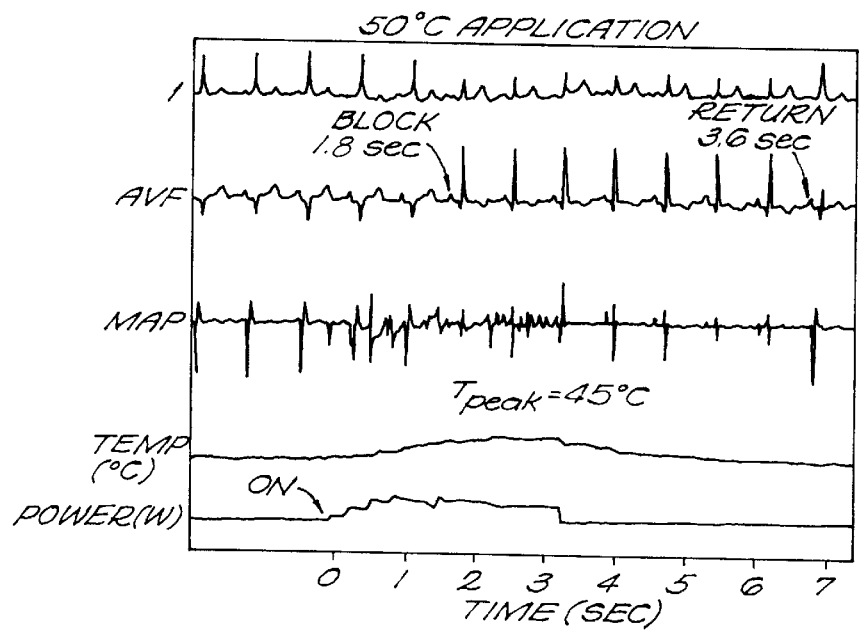
FIGS. 2A and 2B illustrate cardiac signal traces and representative actuation energy during low temperature and high temperature catheter treatment, respectively, for identifying and ablating a conduction path.

The 50° C. low-temperature application resulted in AP block at 14 of the 15 ultimately successful target sites, indicating a very high true positive predictive rate of 93% (see FIG. 1A and the Table of FIG. 4). Block occurred at time 2.4±1.6 seconds ($t_{block}$) into the test application (range, 1 to 7 seconds), with a peak temperature ($T_{peak}$) of 46±1.9° C. (range, 44° C. to 49° C.). Representative cardiac traces and an electrode signal trace are shown in FIG. 2A for one of the test applications. In this particular test application, the radiofrequency generator was set to 50° C. at a rate of 25 mm/s. The maximum temperature achieved was 45° C. and accessory pathway (AP) conduction block occurred after 1.8 seconds. The power was turned off after 3.1 second and AP conduction 3.6 seconds thereafter. AP block occurred at <5 seconds for 13 of the 14 applications (93%). Radiofrequency power was turned off ($t_{off}$) 1.9±0.9 seconds (range, 1.1 to 3.8 seconds) after evidence of AP block, and AP conduction returned for 13 of the 14 pathways (93%) quickly, at 3.1±1.9 seconds (range, 0.7 to 7 seconds) after the power was turned off. This time is denoted $t_{return}$, in FIG. 2A.

The only successful target site that did not block with the 50° C. low-temperature test also failed to block after 8.4 seconds of a 10-second 60° C. test with a $T_{peak}$ of 58° C. (Table of FIG. 4, application no. 6). Conduction resumed 1.8 seconds after the power was turned off. The only low-temperature test that resulted in AP block that was still persistent after 15 minutes was associated with a long delay between AP block and power termination ($t_{off}-t_{block}=3.5$ seconds) (Table of FIG. 4, application no. 5).

Figures 2B, 3:
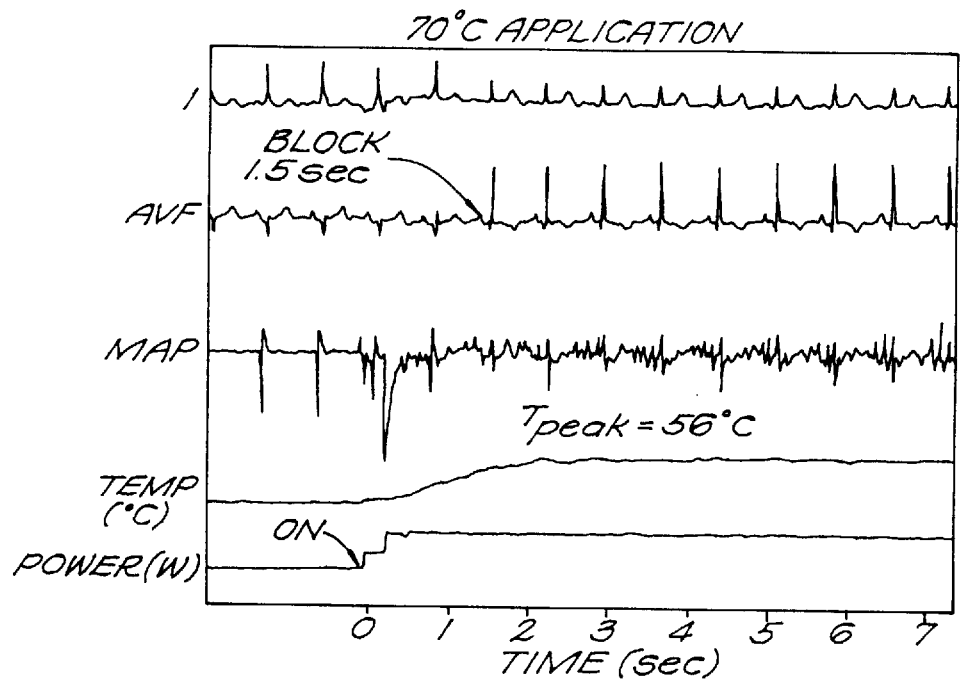
FIG. 3 illustrates tissue damage results with ablation targeting of the present invention.

After either return of conduction (n=14) or 15 minutes (n=1), a radiofrequency application with a set point of 70° C. was delivered for 40 to 60 seconds at all 15 successful sites. A representative ablative RF treatment is illustrated, with cardiac signal and catheter temperature traces, in FIG. 2B. In this particular application, the radiofrequency generator was set to 70° C. and a full application was delivered after the return of AP conduction. The peak temperature ($T_{peak}$) achieved was 56° C. and AP conduction block occurred at 1.5 seconds. The trace labeled I corresponds to a reference signal with the bar indicating 1000 ms intervals. The trace labeled AVF corresponds to the augmented VF as measured from a surface ECG lead and the trace labeled MAP corresponds to the mapping electrical signal. Permanent conduction block occurred at a time $t_{block}$ of 1.3±0.4 seconds (range, 0.7 to 2.1 seconds) and at a $T_{peak}$ of 61 +6° C. (range, 52° C. to 72° C.). The $t_{block}$ for the 70° C. applications was significantly lower than that for the 50° C. test applications (P<0.05), and the $T_{peak}$ was significantly higher (P<0.001). All patients remained free of evidence of AP function at 6 to 11 months of follow-up (median=7 months).

Unsuccessful Sites

At twelve unsuccessful target sites, the 10-second 50° C. test application achieved a $T_{peak}$ of 47±1.9° C. (range, 44° C. to 50° C.; P=NS versus successful sites), resulting in no block for 11 and transient block for 1(see the Table of FIG. 4, and FIG. 1B). A 60° C. test application delivered to 6 of the 11 sites where a 50° C. test failed also failed to achieve block, with a $T_{peak}$ of 54±4.5° C. (range, 49° C. to 62° C.; P<0.002 versus $T_{peak}$ of 50° C. test at the same site). At the one site with transient block, $t_{block}$ occurred at 6.4 seconds with a $T_{peak}$ of 46° C. A 60-second 70° C. application at the same site yielded a lower $t_{block}$ of 3.3 seconds with a peak temperature of 53° C., but conduction returned after an additional 12 seconds.

Summary

In summary, of the 15 tests at 50° C. that caused AP conduction block, 14 of 15 were predictive of successful permanent ablation at that site (positive predictive value, 93%). Furthermore, at 15 ultimately successful target sites, the initial 50° C. test resulted in conduction block in 14 (sensitivity, 93%). Because a 60-second 70° C. application was not delivered at the site of unsuccessful test applications, an accurate negative predictive value and specificity cannot be computed; however, 92% (11 of 12) of the 50° C. tests that did not cause conduction block were delivered at ultimately unsuccessful sites. Finally, the AP conduction block achieved with a short 50° C. test was transient in 14 of 15 instances, indicating that the low-temperature targeting application was non-damaging.

Discussion and Interpretation of Low-Temperature Tests

It is known from various studies of RF energy application to myocardium that catheter electrode-tissue interface temperature is linearly related to lesion dimension, and from tissue damage studies that tissue temperatures in the range of 48° C. to 51° C. can result in reversible electrophysiological effects. Based on these observations, applicants undertook to determine the utility of using a temperature-controlled RF catheter ablation system to minimize myocardial damage while still achieving block, and to assess the accuracy of electrophysiological mapping of AP locations in humans under these low-temperature conditions. The results of EXAMPLE 1 indicate, first, that a brief low-temperature test radiofrequency application that causes AP conduction block predicts.permanent success when a higher-temperature application is delivered to the same site, while a 10-second low-temperature radiofrequency application that does not cause AP conduction block is also highly predictive of failure when a higher-temperature application is delivered to the same site (six of seven cases in this study, as appear in the Table of FIG. 4). Second, with a closed-loop temperature-controlled system, the time to achieve conduction block appears to be a function of the temperature set point, either because the tissue temperature required to achieve block is reached earlier or because a stronger radiofrequency field leads to block at a lower temperature. Finally, brief low-temperature applications produce reversible conduction block, suggesting that the cellular injury is transient. Together, these findings indicate that low-temperature test applications offer improved utility for mapping AP locations while minimizing myocardial damage.

The study of EXAMPLE 1 demonstrates that tip temperatures of 44° C. to 49° C. as measured with a thermocouple embedded centrally in the tip can cause reversible AP block. Generally, electrode-tissue interface temperatures may be 2° C. to 8° C. higher than embedded-tip temperatures, with the difference linearly related to the tip temperature over the range of 45° C. to 75° C. Extrapolation of known data to the test lesions in EXAMPLE 1 would predict a difference of about 2° C. to 2.5° C. between that sensed by the embedded thermocouple and the actual electrode-tissue interface temperatures. In the only published in vivo comparison of multiple simultaneous temperature measurements known to applicants, McRury et al (1995) compared temperatures at four thermistors embedded radially around a catheter tip with the temperature of a thermistor embedded at the tip and concluded that tip temperature was a reasonable measure of electrode-tissue interface temperature, regardless of catheter position or orientation. Although a recent report by Mackey et al (1995) using thermocouples embedded in the tissue has suggested that tissue temperatures may be as much as 44° C. higher than the temperatures at the electrode-tissue interface, others using either fluoroptic temperature probes or thermistors have found that electrode-tissue interface temperatures are generally higher than those at $\geq 1$ mm into the tissue. Finally, both theoretical finite-element temperature distributions and experimental distributions measured with optical thermometry in "tissue-equivalent media" have demonstrated that peak temperatures occur within 0.25 mm of the electrode-tissue interface.

On the basis of the above considerations. a conservative estimate of a difference of 2° C. to 8° C. between the tip and tissue temperatures in this study would yield tissue temperatures of 46° C. to 57° C. during the 50° C. test, including the entire zone of reversible injury (49° C. to 52° C) and the zone of irreversible injury (52° C. to 54° C). Since temperature falls off inversely with distance from these low maximal temperatures, one can deduce that AP block during a low-temperature test application indicates close proximity between the tip and the AP. The high coincidence between predicted and confirmed sites in the above example supports this conclusion. It is also noteworthy that the higher temperatures induced by the 60° C. test applications did not usually cause AP block when a low-temperature 50° C. test had failed, suggesting that inaccurate catheter positioning rather than inadequate heating was responsible for the absence of AP block.

On the basis of a number of previous studies demonstrating that the time to reach half the ultimate lesion dimensions ($t_{1/2}$) is between 6 and 12 seconds, it may be estimated that the typical 70° C. test application applied for 10 seconds creates a significant lesion with a depth of 1 to 3 mm and a width of 2 to 5 mm. In contrast, the short 50° C. test applications in this study should have caused much less, if any, permanent damage, consistent with their transient effect on AP conduction. Thus, the use of a 50° C. test application is expected to identify most sites of at which AP block would not occur, and thus avoid late effects of radiofrequency scar formation from test applications at these sites. This was confirmed by a second study discussed below in connection with EXAMPLE 2 and FIG. 3, in which the low temperature applications were found to cause little or no damage, while 70° C. applications caused significant lesions at most sites.

As shown in FIG. 4, at successful sites, $t_{block}$ was significantly longer for the 50° C. test applications than for the 70° C. applications at the same site, suggesting that the time required to achieve AP block is a function of tissue temperature. Lesion size is determined, among other factors, by the duration of the application. At the successful sites, $t_{block}$ occurred in <5 seconds for 93% of the 50° C. tests. For the 12 unsuccessful sites, there was only a single false-positive 50° C. test, and it caused AP block at a $t_{block}$ of 6.4 seconds. Finally, the only 50° C. test that resulted in prolonged AP block (>15 minutes) was continued for a total of 6.2 seconds. These observations support a hypothesis that a shorter test application of 5 seconds would generally be sufficient to achieve AP block, while minimizing false-positive results and also further minimizing tissue damage. It should be noted that when an atrial approach is used for ablation of APs, the generator set temperature is rarely achieved even with closed-loop feedback control of power output. However, with the lower set point in the study of EXAMPLE 1, a temperature within 6° C. of the 50° C. target was achieved for all successful and unsuccessful test applications. However, the precise physiological effects of the 50° C. test application are not certain. Since there was no independent measurement of tissue damage in EXAMPLE 1, that study alone does not conclusively demonstrate the absence of damage induced by the brief low-temperature applications. As noted above, tissue temperatures were probably higher than the $T_{peak}$ measured at the catheter tip. However, when previous experimental data are combined with the observation of rapid reversible electrophysiological effects after the test applications, it is highly likely that tissue damage was less than that resulting from standard techniques. Finally, firm conclusions regarding the adequacy of unsuccessful 50° C. test applications for predicting failure with a higher temperature application at a particular site are limited by the statistical power, the study design and protocol deviations; however, the data do demonstrate that success is unlikely at sites where a 50° C. test does not cause conduction block.

In order to assess whether any physical damage is incurred by the 5- or 10-second low temperature mapping protocol of the present invention, as second series of in vivo applications was carried out in animals to better correlate or confirm the tip thermal set point conditioner with previous in vitro tissue thermal measurements. The results of this trial are set forth in EXAMPLE 2.

EXAMPLE 2

A series of RF energy applications were performed at 50° C., 60° C., and 70° C. set points for ten seconds in six sheep (50° C., n=2; 60° C., n=2 70° C. n=2) using a temperature-controlled catheter ablation system as described above. Each animal underwent placement of 18 intended transcatheter lesions (three in each atrium (A), three on each atrioventricular (AV) groove, and three in each ventricle (V)).

Temperature, power, and impedance were recorded. The sites were then inspected for lesions, and the lesions were measured for largest endocardial and epicardial dimensions, and depth. Lesion volumes were calculated based on the volume of a prolate sphere: ½×4/3×π×depth×lesion radius. The results are summarized in FIG. 3 for the three regions at the three set points employed. As shown in that FIGURE, less than 10% of the RF applications at 50° C. resulted in lesions, a significantly lower rate than at either 60° C. or 70° C. In addition, lesions from 50° C. applications that did occur were significantly smaller than those made at the higher temperatures. Neither yield nor lesion size differed between 60° C. and 70° C. The overall depth×lesion radius of 0.5–1.0 mm³ at those ten percent of sites where 50° C. lesions were detected was quite small.

As noted above, applicants anticipate that the use of a five second $t_{off}$ interval rather than the ten second regimen employed in EXAMPLE 2 will reduce the already low incidence of false positives, and this may be expected to further reduce or eliminate the formation of detectable lesions at the low temperature test applications.

Thus, applicants' low temperature RF target site confirmation method determines suitable AP block sites, with both a high true positive and low false negative predictive value, and does so in a substantially a traumatic manner using currently available equipment. This equipment is readily modified to operate at two set point temperatures with a short maximum time at the lower set point, and advance to the higher set point being triggered only upon detection of AP block.

The invention being thus disclosed and described, adaptation of the protocols and system to diverse ablation procedures and equipment, and implementation of the invention by suitable programming, connection or modification of ablation equipment, as well as other variations and modifications thereof, will occur to those skilled in the art. All such adaptations, variations and modifications are considered to be within the scope of the invention, as set forth in the claims appended hereto and equivalents thereof.

What is claimed is:

1. A method of cardiac ablation to selectively ablate a conduction pathway, such method comprising the steps of inserting an ablation catheter to a potential target site in the heart, said ablation catheter having at least one treatment electrode, actuating the treatment electrode with a first actuation to heat tissue at the potential target site to a non-damaging temperature below about 52° C., monitoring the temperature of the potential target site to maintain the temperature of the potential target site at the non-damaging temperature for a time effective to temporarily and reversibly block conduction in a local region about the treatment electrode, monitoring cardiac signals to determine if the first actuation achieved conduction block, and if so then subsequently, and actuating the treatment electrode with a second actuation effective to locally ablate tissue and create an irreversible conduction block.

2. The method of claim 1, wherein said non-damaging temperature is a temperature between about 48°–52° C.

3. The method of claim 1, wherein the step of monitoring includes operating the electrode under feedback control based on the temperature measured by a temperature sensor attached to said catheter.

4. The method of claim 1, wherein the steps of actuating with a first actuation and with a second actuation is performed by a catheter controller having first and second set points, said controller being responsive to an actuation signal for proceeding to said second actuation at said second set point.

5. The method of claim 4, wherein said actuation signal is manually triggered.

6. The method of claim 4, wherein said actuation signal is automatically triggered responsive to detection of the occurrence of conduction block at said first set point.

7. The method of claim 1, wherein the time effective to temporarily and reversibly block conduction in a local region is less than or equal to about 10 seconds.

8. A method of positioning an ablation catheter at an arrhythmia site to apply ablative power thereto, such method comprising the steps of positioning an ablation catheter at a likely arrhythmia site in a patient's heart, applying a non-ablating level of energy to said ablation catheter in an amount effective to heat a region adjacent the ablation catheter to a non-damaging temperature below about 52° C. to temporarily and reversibly block conduction in the region monitoring cardiac signals to detect an arrhythmia signal associated with said likely site, and in the event conduction block is not achieved, repeating the steps of positioning and applying non-ablating energy until conduction block is achieved thereby confirming placement of the catheter in a position to effectively ablate the arrhythmia site.

9. The method of claim 8, further comprising the step of mapping an location of the confirmed catheter position.

10. The method of claim 8, further comprising the step of applying an ablating level of energy to achieve a tissue temperature in the range of 60°–70° C. at the confirmed catheter position.

11. A method of targeting a cardiac ablation site, such method comprising the steps of applying a non-damaging level of energy from an RF catheter to the site for a targeting time t, said time t being sufficiently long to locally achieve at least temporarily AP conduction block and sufficiently short to avoid non-local AP conduction block, and detecting when a local AP conduction block occurs to identify a target site for ablation.

* * * * *